US00PP25703P2

(12) United States Plant Patent
Nazeyrollas

(10) Patent No.: US PP25,703 P2
(45) Date of Patent: Jul. 14, 2015

(54) ***DEUTZIA* PLANT NAMED 'MINCREAM'**

(50) Latin Name: *Deutzia gracilis*
Varietal Denomination: Mincream

(71) Applicant: Olivier Nazeyrollas, Beaufort en Vallee (FR)

(72) Inventor: Olivier Nazeyrollas, Beaufort en Vallee (FR)

( * ) Notice: Subject to any disclaimer, the term of this patent is extended or adjusted under 35 U.S.C. 154(b) by 88 days.

(21) Appl. No.: 13/987,830

(22) Filed: Sep. 6, 2013

(51) Int. Cl.
*A01H 5/00* (2006.01)

(52) U.S. Cl.
USPC ..... Plt./226

(58) Field of Classification Search
USPC ..... Plt./226
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Deutzia* plant named 'Mincream', characterized by its compact, low spreading to trailing plant habit; variegated leaves that are green and pale yellow in color; freely flowering habit; white-colored flowers; and good garden performance.

2 Drawing Sheets

Botanical designation: *Deutzia gracilis.*
Cultivar denomination: 'MINCREAM'.

BACKGROUND OF THE INVENTION

The present invention relates to a new and distinct cultivar of *Deutzia* plant, botanically known as *Deutzia gracilis* and hereinafter referred to by the name 'Mincream'.

The new *Deutzia* plant is a naturally-occurring branch mutation of an unnamed proprietary selection of *Deutzia gracilis*, not patented. The new *Deutzia* plant was discovered and selected by the Inventor on a single plant of the proprietary selection in a controlled outdoor nursery environment in La Ménitré, Maine et Loire, France in July, 2002.

Asexual reproduction of the new *Deutzia* plant by cuttings in a controlled greenhouse environment in La Ménitré, Maine et Loire, France since August, 2002 has shown that the unique features of this new *Deutzia* plant are stable and reproduced true to type in successive generations of asexual reproduction.

SUMMARY OF THE INVENTION

Plants of the new *Deutzia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Mincream'. These characteristics in combination distinguish 'Mincream' as a new and distinct *Deutzia* plant:

1. Compact, low spreading to trailing plant habit.
2. Variegated leaves that are green and pale yellow in color.
3. Freely flowering habit.
4. White-colored flowers.
5. Good garden performance.

Plants of the new *Deutzia* differ primarily from plants of the unnamed proprietary parent selection in leaf color as plants of the unnamed proprietary parent selection have non-variegated leaves.

Plants of the new *Deutzia* can also be compared to plants of *Deutzia longifolia* 'Aurea', not patented. In side-by-side comparisons conducted in La Ménitré, Maine et Loire, France, plants of the new *Deutzia* and 'Aurea' differed primarily in the following characteristics:

1. Plants of the new *Deutzia* were more compact than plants of 'Aurea'.
2. Plants of the new *Deutzia* were low spreading to trailing whereas plants of 'Aurea' were upright.
3. Plants of the new *Deutzia* and 'Aurea' differed in leaf color as plants of 'Aurea' had green and darker yellow variegated leaves.
4. Leaves of plants of the new *Deutzia* did not sunburn under full sunlight conditions whereas leaves of plants of 'Aurea' sunburned under full sunlight conditions.

BRIEF DESCRIPTION OF THE PHOTOGRAPHS

The accompanying colored photographs illustrate the overall appearance of the new *Deutzia* showing the colors as true as it is reasonably possible to obtain in colored reproductions of this type. Colors in the photographs may differ slightly from the color values cited in the detailed botanical description which accurately describe the colors of the new *Deutzia*.

The photograph on the first sheet comprises a side perspective view of a typical plant of 'Mincream' grown in a container.

The photograph on the second sheet is a close-up view of a typical flowering plant of 'Mincream'.

DETAILED BOTANICAL DESCRIPTION

The aforementioned photographs and following observations, measurements and values describe plants grown in one-gallon containers during the summer in an outdoor nursery in Grand Haven, Mich. and under commercial production practices. Plants were two years old when the photographs and description were taken. In the following description, color references are made to The Royal Horticultural Society Colour Chart, 2001 Edition, except where general terms of ordinary dictionary significance are used.

Botanical classification: *Deutzia gracilis* 'Mincream'.

Parentage: Naturally-occurring branch mutation of an unnamed proprietary selection of *Deutzia gracilis*, not patented.

Propagation:

*Type*.—By cuttings.

*Root description*.—Fibrous, medium in thickness; white in color.

*Rooting habit*.—Moderate branching; moderately dense.

Plant description:

*Plant form and habit*.—Compact, low spreading to trailing plant habit; vigorous growth habit.

*Branching habit*.—Freely branching habit with about 18 lateral branches developing per plant.

*Plant height*.—About 25 cm.

*Plant width* (*spread*).—About 35 cm.

*Lateral branches*.—Length: About 15 cm. Diameter: About 3 mm. Internode length: About 1 cm. Strength: Strong. Texture: Smooth, glabrous. Color: Close to 197B.

Leaf description:

*Arrangement*.—Opposite, simple.

*Length*.—About 4 cm.

*Width*.—About 1.5 cm.

*Shape*.—Lanceolate.

*Apex*.—Acute.

*Base*.—Obtuse.

*Margin*.—Serrulate.

*Texture, upper and lower surfaces*.—Pubescent.

*Venation pattern*.—Pinnate.

*Color*.—Developing leaves, upper and lower surfaces: Center, close to 147B; border, close to 160D and 158B. Fully developed leaves, upper and lower surfaces: Center, close to 146A; border, close to 11D; venation, close to 147D.

*Petioles*.—Length: About 5 mm. Diameter: About 1 mm. Texture, upper and lower surfaces: Pubescent. Color, upper and lower surfaces: Close to 147C.

Flower description:

*Flower type and flowering habit*.—Single rotate flowers arranged in terminal panicles; flowers face outwardly to drooping; freely flowering habit with about 32 flowers developing per inflorescence.

*Fragrance*.—None detected.

*Natural flowering season*.—Continuously flowering for about three to six weeks during the late spring in Michigan; flowers not persistent.

*Flower buds*.—Height: About 5 mm. Diameter: About 3 mm. Shape: Oblong to elliptical. Color: Close to 155D.

*Inflorescence height*.—About 6 cm.

*Inflorescence diameter*.—About 3 cm.

*Flower diameter*.—About 1.5 cm.

*Flower depth*.—About 1 cm.

*Petals*.—Quantity per flower: Typically five in a single whorl. Length: About 1 cm. Width: About 5 mm. Shape: Ovate to oblong. Apex: Acute. Margin: Entire. Texture, upper and lower surfaces: Smooth, glabrous. Color: Developing petals, upper and lower surfaces: Close to 155D. Fully developed petals, upper and lower surfaces: Close to 155D.

*Sepals*.—Quantity per flower: Typically five in a single whorl, fused towards the base. Length: About 2 mm. Width: About 1 mm. Shape: Ovate. Apex: Acute. Margin: Entire. Texture, upper and lower surfaces: Smooth, glabrous. Color: Developing sepals, upper and lower surfaces: Close to 146A; towards the apex, close to 158B. Fully developed sepals, upper and lower surfaces: Close to 146A; towards the apex, close to 158B.

*Peduncles*.—Length: About 2 cm. Diameter: About 0.7 mm. Strength: Strong. Texture: Smooth, glabrous. Color: Close to 146C.

*Pedicels*.—Length: About 4 mm. Diameter: About 0.5 mm. Strength: Strong. Texture: Smooth, glabrous. Color: Close to 146C.

*Reproductive organs*.—Stamens: Quantity per flower: Typically ten. Anther shape: Round. Anther length: About 0.5 mm. Anther color: Close to 12C. Pollen amount: Moderate. Pollen color: Close to 12C. Pistils: Quantity per flower: Three to five. Pistil length: About 4 mm. Stigma shape: Round. Stigma color: Close to 155D. Style length: About 4 mm. Style color: Close to 155D. Ovary color: Close to 146A.

*Seeds*.—Size: Minute, dust-like. Color: Brownish.

Disease & pest resistance: Plants of the new *Deutzia* have not been observed to be resistant to pathogens or pests common to *Deutzia* plants.

Garden performance: Plants of the new *Deutzia* have been observed to have good garden performance.

It is claimed:

1. A new and distinct *Deutzia* plant named 'Mincream' as illustrated and described.

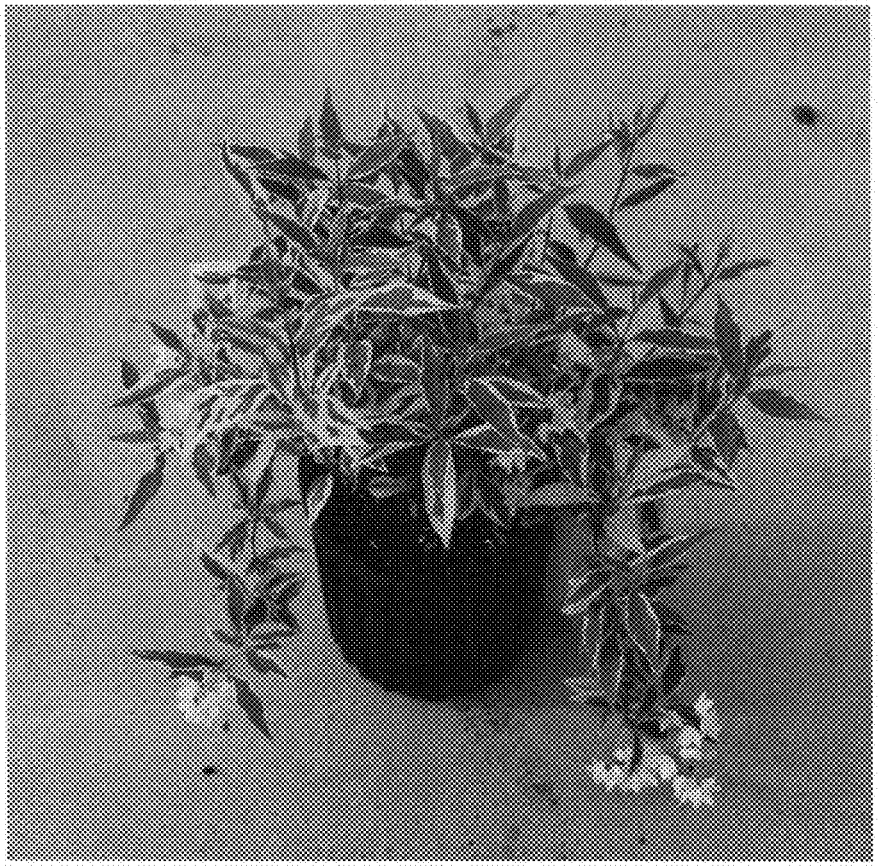

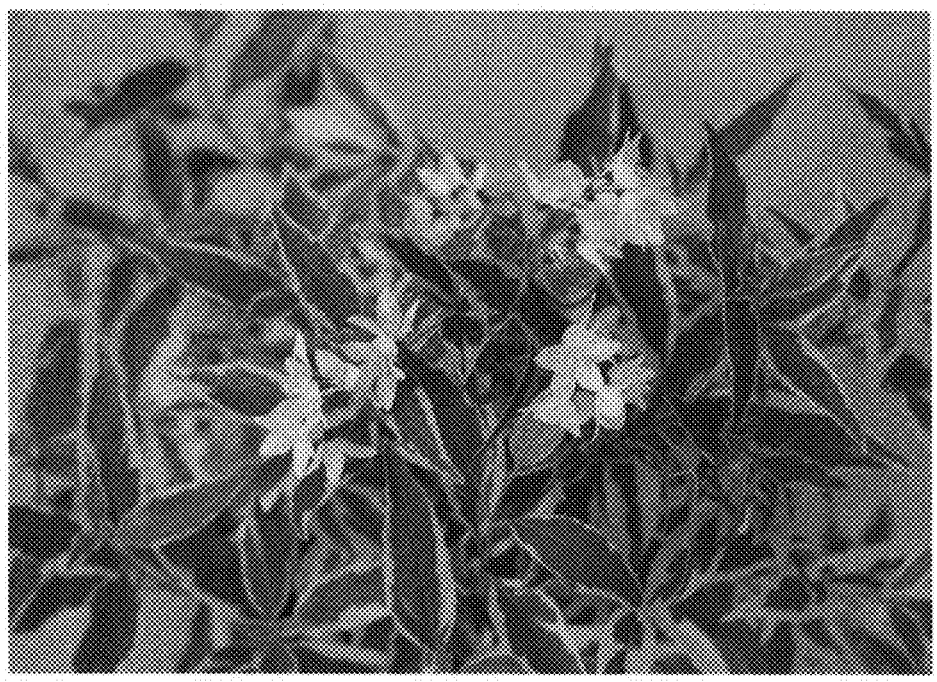

* * * * *